United States Patent [19]

West et al.

[11] Patent Number: 5,268,518

[45] Date of Patent: Dec. 7, 1993

[54] REACTOR FEED PIPE DESIGN

[75] Inventors: David H. West; Lawrence A. Hebert; Stanford S. Kirsch, all of Baton Rouge, La.

[73] Assignee: The Dow Chemical Company, Midland, Mich.

[21] Appl. No.: 32,565

[22] Filed: Mar. 17, 1993

Related U.S. Application Data

[63] Continuation of Ser. No. 792,830, Nov. 15, 1991, abandoned.

[51] Int. Cl.$^5$ .............................................. C07C 17/10
[52] U.S. Cl. ...................................... 570/255; 570/252
[58] Field of Search ................................. 570/252, 255

[56] References Cited

U.S. PATENT DOCUMENTS

| | | | |
|---|---|---|---|
| 2,591,700 | 4/1952 | Jacolev et al. | 252/373 |
| 2,806,768 | 9/1957 | Bender et al. | 570/255 |
| 2,904,417 | 9/1959 | Te Nuyl | 252/373 |
| 2,989,571 | 6/1961 | Eisenlohr | 570/255 |
| 3,054,831 | 9/1962 | Samples et al. | . |
| 3,505,418 | 4/1970 | Jubin | 570/252 |
| 3,522,017 | 7/1970 | Barfield, Jr. | . |
| 4,590,044 | 5/1986 | Mos et al. | 422/191 |
| 5,023,387 | 6/1991 | West et al. | 570/252 |

OTHER PUBLICATIONS

Latornell, et al., "Some Observations on the Evolution of Shear Layer Instabilities in Laminar Flow Through Axisymmetric Sudden Expansions," *Phys. Fluids*, Sep. 1986, pp. 2828-2835.

*Primary Examiner*—Howard T. Mars

[57] ABSTRACT

Process and apparatus for enhancing entrainment and self-stirring adjacent the entry of a reactor vessel of at least partly-reacted materials in an incoming stream of reactants.

5 Claims, 2 Drawing Sheets

REACTOR FEED PIPE DESIGN

CROSS-REFERENCE TO RELATED APPLICATION

This is a continuation application Ser. No. 07/792,830, filed Nov. 15, 1991 now abandoned.

BACKGROUND OF THE INVENTION

This is a continuation of application Ser. No. entrainment-controlled mixing of products and reactants is important, and to the feed pipes and nozzles used in such reactors for feeding reactants thereto. More particularly, but without limitation, the present invention relates to reactors and feed pipes and nozzles for the production of chloromethanes and other useful chlorinated derivatives by thermally-initiated adiabatic, vapor-phase chlorination.

Typically chloromethanes and these other chlorinated derivatives are produced in a gas phase chlorination reactor apparatus which consists of a pipe feeding into a larger diameter vessel. Chlorine and organic reactants such as methyl chloride and methylene chloride are premixed in the feed pipe, and fed into the larger vessel at high velocities but at temperatures which are insufficient to initiate the chlorination reaction. Hot, already reacted product gases are entrained into the high velocity feed stream as the stream expands into the reactor and moves along the reactor's length, however, and provide the necessary heating to initiate and propagate the chlorination reaction. As reactants continue to be fed into the reactor, hot product gases are continuously recirculated back toward the inlet of the reactor in a "self-stirring" mechanism.

A primary goal in the design of any high temperature, vapor-phase chlorination reactor apparatus, or in the retrofitting of an existing apparatus, thus is to ensure that adequate self-stirring of the products and reactants occurs in the reactor. In general, though, the amount of entrainment and recirculation that can be achieved in a typical sudden expansion-type reactor apparatus, as by using a smaller nozzle to create higher feed velocities, is limited.

Achieving a greater degree of recirculation and self-stirring would have a couple of very significant benefits. Unreacted chlorine tends to have a significant corrosive effect, and greater recirculation and self-stirring improve the chlorine conversion over a reactor of a given length so that less corrosion of downstream equipment occurs. In addition, improved self-stirring increases the critical flowrate at which the reaction is quenched or "blown out". At high reactant flow rates, the rate of heat removal by convection may exceed the rate of heat generation by reaction of the incoming reactants. Improved self-stirring feeds back more of the heat of reaction to the incoming reactants.

The chlorination reactor art reveals several attempts at achieving greater mixing of products and reactants. For example, in U.S. Pat. No. 3,054,831 to Samples et al. a halogen gas such as chlorine is fed into a reactor through a jet nozzle, which jet nozzle in turn feeds into a venturi tube. The venturi tube is provided with ports or is open at its upper end so that hydrocarbon reactant and hot product gases from the reactor can be drawn into and through the venturi by the passage therethrough of the high velocity chlorine gas from the jet nozzle. The hydrocarbon reactant is fed tangentially into the reactor through an inlet pipe at about the level of the discharge end of the venturi.

In U.S. Pat. No. 3,522,017 to Barfield, Jr., a similar device is disclosed in which the several gaseous reactants are premixed and discharged through an actuating nozzle threaded into a bottom wall of the reactor. The actuating nozzle tapers down to a small cross-section and discharges the premixed reactant gases at high velocity into a larger diameter, slightly inwardly tapering tube, the tube being preceded however by inlet slots or ports so that reactant and product gases already in the vessel can be entrained in the high velocity gas stream from the actuating nozzle. The tube delivers the gases into a diffuser/expander which divergently sprays the gases into the reactor volume.

And in U.S. Pat. No. 4,590,044 to Mos et al., a first reactant in traveling a zigzag path through successive reactor stages is contacted in some stages by a cross-currently injected second reactant at a high temperature and a high velocity, and in other stages by opposed high velocity, cross-currently injected high and low temperature streams of the second reactant. Effective mixing of the first and second reactants and of formed products is said accomplished by the differences in velocity of the first and second reactant streams into the reaction space.

The primary drawbacks of these other devices are their complexity and expense of manufacture compared to a sudden expansion-type reactor, and the related difficulty or impossibility of practically and economically applying the features of these devices to retrofitting and upgrading an existing chlorination reactor apparatus.

SUMMARY OF THE INVENTION

The present invention meets the needs not met by the prior art, and enables improved recirculation and self-stirring in both new reactors and especially in retrofitting existing reactors, without being overly complex to make or to install in an existing reactor.

The present invention in one aspect relates broadly to a process for enhancing the entrainment adjacent the entry end of a reactor vessel of at least partly-reacted materials in an incoming stream of reactants, by disrupting the flow pattern of the incoming stream of reactants upstream of the reactants' entry into the reactor vessel. In a more particularized context, entrainment and self-stirring is enhanced in a thermally-initiated, adiabatic vapor-phase chlorination reactor apparatus, and especially an apparatus of the sudden expansion type.

In a second broad aspect of the present invention, a self-stirred reactor apparatus is provided which comprises: a reactor vessel; a feed pipe through which a stream of two or more reactants enters the reactor vessel; and means placed in said feed pipe for disrupting the flow pattern of the incoming stream of reactants upstream of the reactants' entry into the reactor vessel, whereby self-stirring is improved in the reactor vessel. In a more particularized context, apparatus are provided which display improved self-stirring and entrainment for the thermally-initiated, adiabatic vapor-phase chlorination of organics.

DETAILED DESCRIPTION OF THE PREFERRED EMBODIMENTS

Figure 1:
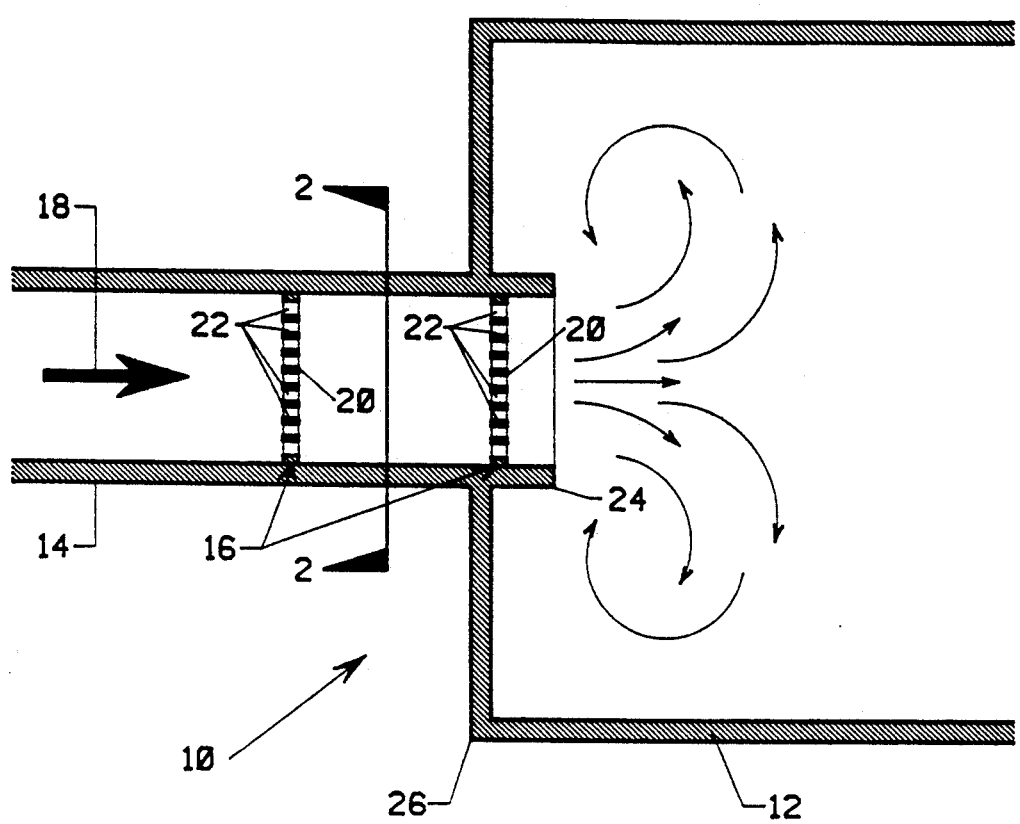
FIG. 1 is a partial cross-sectional view of a reactor apparatus of the present invention in one preferred embodiment.
Figure 2:
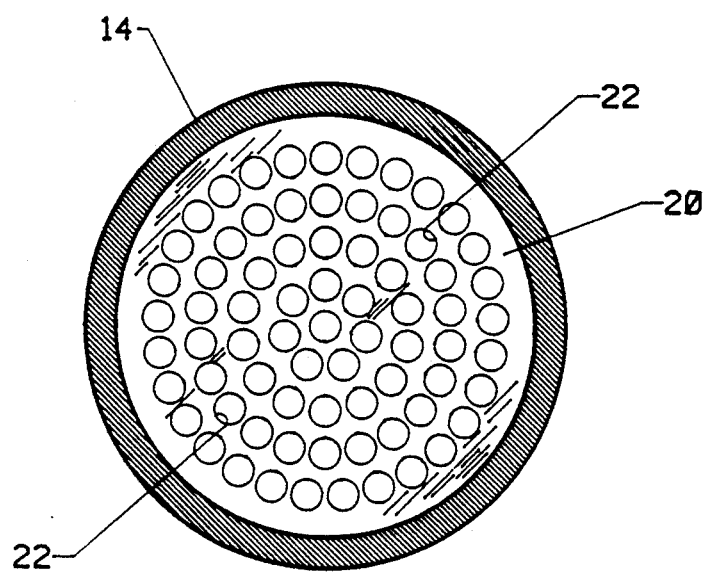
FIG. 2 is an end view, taken from the perspective of line 2—2 of FIG. 1, of the means employed for disrupting the flow pattern of a stream of reactants in the feed pipe of the apparatus of FIG. 1.

Referring now to the drawings, and more particularly to FIGS. 1 and 2, a first preferred embodiment 10 of a reactor apparatus of the present invention is illustrated.

The reactor apparatus 10 represents in most respects a typical chlorination reactor apparatus of the "sudden expansion" or "sudden enlargement" self-stirring type, and broadly comprises a reactor vessel 12 which is generally in the form of a large cylindrical pipe capped at the ends, a smaller, tubular feed pipe 14, and means 16 placed across and in the feed pipe 14 for disrupting the flow pattern of an incoming stream 18 of reactants upstream of their entry into reactor vessel 12.

As with conventional "sudden expansion" type chlorination reactors, the diameter of the vessel 12 is generally from about 1.5 to about 15 times, preferably is from about 3 to about 10 times, and most preferably is from about 4 to about 8 times the diameter of the feed pipe 14. Other features of the reactor apparatus 10, with the exception of the addition in the present invention of flow disrupting means 16, may likewise be of a similar construction to conventional reactors. Preferably the apparatus 10 will operate according to known thermally-initiated, adiabatic vapor phase chlorination processes such as described in U.S. Pat. No. 3,054,831 to Samples et al., in Kirk-Othmer Encyclopedia of Chemical Technology, 3rd edition, Vol. 5, John Wiley and Sons (1979) at from pages 680 through 698, and in U.S. Pat. No. 5,023,387 to West et al., with the last, West et al. patent hereby being incorporated herein by reference.

A critical aspect of these types of processes and apparatus is, as indicated above, the sell-stirring by entrainment of partially reacted product gases into the stream of reactant gases entering the reactor vessel 12. Those skilled in the art will appreciate that in typical "sudden expansion"-type chlorination reactors, using a smaller diameter feed pipe increases the rate of recirculation adjacent the vessel's entry end (or upstream end), but at a certain point additional constriction of the feed line reduces the overall rate of chlorination because of reduced downstream pressures of chlorine and the organic reactant or reactants, or increases the upstream pressure required to obtain a given flowrate through the vessel.

The principal contribution of the present invention is in increasing turbulence and self-stirring or recirculation in a reactor vessel without significantly increasing the pressure drop associated with a given diameter feed pipe. Higher reactant feed rates can then be employed without quenching the reaction and/or so that a greater conversion of chlorine can be achieved in a reactor to minimize corrosion in downstream process equipment, all without the extensive or complex fabrication or modification associated with and necessitated by the devices shown in U.S. Pat. No. 3,054,831 to Samples et al., 3,522,017 to Barfield, Jr., and 4,590,044 to Mos et al.

This increased self-stirring is accomplished through the agency of the flow disrupting means 16, which in FIGS. 1 and 2 comprises a plurality of thin perforated plates 20 positioned across and in the feed pipe 14 upstream of the reactants' entry into the vessel 12.

So that the plates 20 accomplish their function of disrupting the flow pattern of the reactant stream in pipe 14 without significantly increasing the pressure drop from the reactants' entry to the reactants' exit from the reactor vessel 12, and as seen best in FIG. 2, the perforations 22 in plates 20 define a free area of about 20 percent or greater, more preferably about 45 percent or greater, and most preferably define a free area in the plate 20 and across a cross-section of an incoming reactant stream of about 80 percent or greater. At the same time, this free area is preferably substantially evenly distributed throughout a cross-section of the incoming reactant stream, for example by employing identically-sized perforations 22 which are evenly distributed in a plate 20.

A "significant" increase in the pressure drop from the reactants' entry into the vessel 12 to their exit therefrom corresponds, for purposes of the present disclosure, to that level of constriction of the feed pipe 14 and of the reactant stream passing therethrough to which reference was made earlier in regard to a diminished overall rate of chlorination or excessive upstream pressure requirements.

Normally the plate 20 nearest the reactants' entry into the vessel 12 will be located a distance of 0.5 to 5, more preferably 0.5 to 4, and most preferably 0.5 to 2 feed pipe diameters upstream of where the reactants enter the vessel 12 and begin expanding (i.e., at the internal end 24 of the feed pipe 14). Additional plates 20 can be located upstream of this first, downstream plate 20.

The positioning of the plates 20 relative to one another and to the internal end 24 of the feed pipe 14, the nature and distribution of the perforations 22, and the free area defined by such perforations may all be expected however to have some bearing on the manner in which the reactant stream flows into the reactor vessel 12 and on the degree of self-stirring achieved adjacent the entry end 26 of the reactor vessel 12. Similarly, the use of a single plate 20 may produce a somewhat different effect as compared to a plurality of plates 20.

What arrangements and designs most effectively increase self-stirring in the context of a given chlorination process may be determined by routine experimentation, for example by comparing the degree of chlorine conversion achieved in two apparatus 10 under the same operating conditions but with different arrangements and designs of the plates 20 or some other flow disrupting device or means 16. In general, however, the plates 20 or other means 16 should not involve a significantly increased pressure drop, and should disturb the flow pattern of the reactant stream evenly across the stream's cross-section.

It is presently believed that the most effective designs and arrangements will generally be characterized by certain effects on the flow and flow patterns of the reactant stream entering a vessel 12. As a first guideline, those designs and arrangements which uniformly cause a greater rate of expansion of the reactant stream on entering the vessel 12 should usually be preferred over designs and arrangements which cause a lesser rate of expansion. The zone in which self-stirring occurs, and thus the reaction zone of the vessel 12, is shorter in the former situation than in the latter, leaving a greater length of reactor in which to convert unreacted chlorine in plug-flow fashion.

As a second general guideline, those designs and arrangements which uniformly create a greater degree of turbulence and mixing at the boundaries of an incoming reactant stream, where the partly reacted gases come into contact with and are entrained in the reactant stream, should usually be preferred over designs and arrangements creating a lesser degree of turbulence and mixing at such locations.

Even where in the absence of such plates 20 the incoming stream of reactants would be in a turbulent flow regime at the entry of the stream into the vessel 12, i.e., where the incoming reactant stream is characterized by a Reynolds number of at least about 100,000, the imposition of one or more of the plates 20 or of some similar flow disrupting means 16 can work a surprising improvement in recirculation and self-stirring in the vessel 12 as manifested by residual unreacted chlorine levels.

Figure 3:
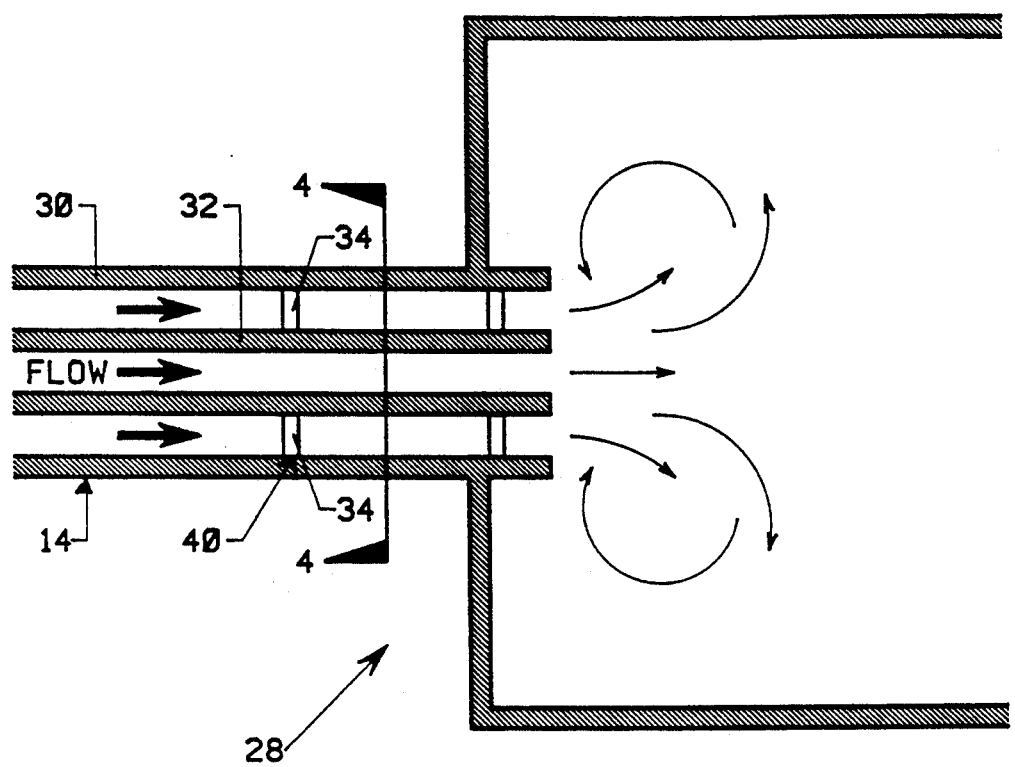
FIG. 3 is a partial cross-sectional view of a reactor apparatus of the present invention in an alternate preferred embodiment.
Figure 4:
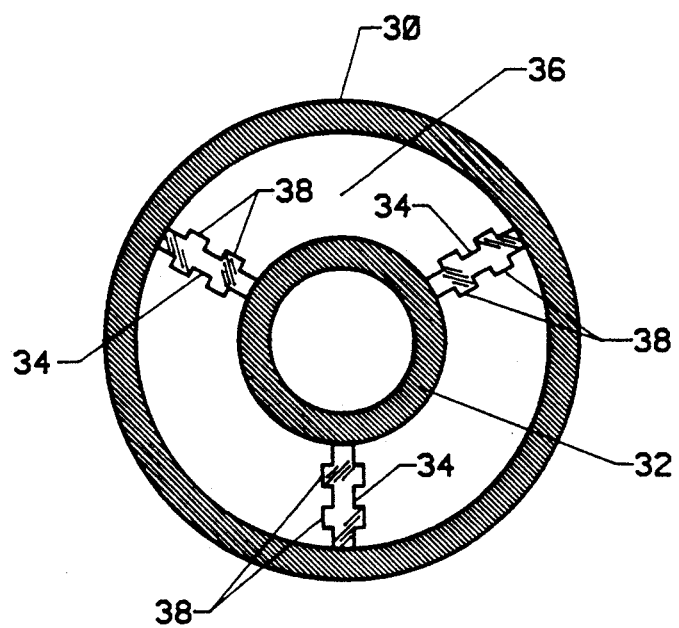
FIG. 4 is an end view, taken from the perspective of line 4—4 of FIG. 3, of the means employed for disrupting the flow pattern of a stream of reactants in the feed pipe of the apparatus of FIG. 3.

An alternate preferred embodiment 28 of the reactor apparatus of the present invention is illustrated in FIGS. 3 and 4, and illustrates the use of a different flow disrupting means 16 with different chlorination process equipment. In the embodiment 28 of FIGS. 3 and 4, the feed pipe 14 is comprised of an outer feed pipe 30 and an interior, coaxial liquid feed pipe 32 supported within the outer pipe 30 by guide vanes 34 spaced around the pipe 32 at intervals. Liquid feed pipe 32 carries a portion, preferably, of the organic reactant or reactants in accordance with the teachings of commonly-assigned U.S. Pat. No. 5,023,387 to West et al., while in the annulus 36 between the inner liquid feed pipe 32 and outer feed pipe 30 flow premixed chlorine and organic reactants (which can be hydrocarbons such as propene or chlorinated hydrocarbons like methyl chloride and methylene chloride) in the gas phase. In more general terms, and with the exception of the flow disrupting means 16, the reactor apparatus 28 as a whole is preferably constructed and operated according to the teachings of the West et al. patent.

The particular flow disrupting means 16 of the apparatus 28 is best shown in FIG. 4, and comprises a plurality of tabs 38 attached to the guide vanes 34. The guide vanes 34 and tabs 38 together define a free area in the annulus 36 of at least about 80 percent, although more preferably the vanes 34 and tabs 38 define a free area of at least about 90 percent and most preferably of at least about 95 percent.

Preferably the tabs 38 are allocated among the guide vanes 34 so that the free area defined by the vanes 34 and tabs 38 together is substantially evenly distributed throughout an incoming stream of reactants and throughout the annulus 36 as shown in FIG. 4. The discussion above concerning the location and spacing of the plates 20 in the embodiment 10 is equally applicable to the spacing and location of sets 40 of tabbed vanes 34 in the apparatus 28, but normally the set 40 of tabbed vanes 34 nearest the reactants' entry into the vessel 12 will be located a distance of 0.5 to 5, more preferably 0.5 to 4, and most preferably 0.5 to 2 feed pipe diameters upstream of the internal end 24 of pipe 14. Additional sets 40 can be located upstream of this first, downstream set 40 of tabbed vanes 34.

It may also be useful to employ combinations of various flow disrupting means 16 in combination, for example in the embodiment 28 by defining the free area in the annulus 36 at one position in the form of evenly spaced perforations 22 around the inner pipe 32, while allocating the free space in the annulus 36 at a second position to the space between a set 40 of tabbed guide vanes 34.

It should be apparent from the foregoing discussion that the present invention could find application in any process wherein the entrainment-controlled mixing of products and reactants is of interest, to the design and fabrication of new reactor apparatus for use in these sorts of processes, or with particular benefits in the simple, inexpensive and effective retrofitting of existing "sudden expansion"-type chlorination reactor apparatus. The present invention possesses a further advantage in retrofitting these existing reactors, too, in that one could conceivably employ the same basic plates 20 and/or sets 40 of tabbed vanes 34 to achieve a variety of backmixing effects and to fill a considerable variety of needs.

The present invention is further illustrated by the following examples:

EXAMPLE 1

In this example, two conventional sudden expansion-type chlorination reactor apparatus involving different degrees of expansion were compared. These otherwise identical production-scale reactors were in the form of a cylindrical pipe capped at either end, with the first reactor having a feed pipe diameter to reactor diameter proportionality of 0.20, and the second reactor having a feed pipe diameter to reactor diameter proportionality of 0.12.

Methyl chloride, methylene chloride and chlorine gases were premixed through a tee placed about 20 feed pipe diameters upstream of each reactor. The premixed reactants were at a temperature of from about 50 to about 100 deg. C., and a pressure of 45 psig. The chlorine in the feed was kept to between 23 and 25 mole percent, while the methyl chloride and methylene chloride were fed to the reactor in a mole ratio of from about 0.5 to about 2.0 (of methyl chloride to methylene chloride). The reactor outlet temperature and the temperature throughout the reactor were kept below about 490 deg. C.

Unreacted chlorine was sensed or measured at the outlet of each reactor apparatus. The first reactor apparatus having a d/D ratio of 0.20 (where d is the feed pipe diameter and D is the reactor diameter) left 120 parts per million by weight of unreacted chlorine in the product stream. By comparison, the second reactor apparatus with a d/D ratio of 0.12 left 20 ppm by weight of unreacted chlorine, so that the lower d/D ratio and greater expansion associated with the second reactor evidently caused a greater degree of recirculation in the reactor and a more complete conversion of the chlorine.

EXAMPLE 2

For this example, a comparison was made between a pilot plant scale (1/350th of the volume of the production-scale reactor apparatus used in Example 1) sudden expansion-type reactor apparatus having a d/D ratio of 0.20 and a pilot plant scale reactor apparatus (hereinafter referred to as a basic gas/liquid reactor apparatus) involving the same degree of expansion, but which was constructed and operated according to the teachings of U.S. Pat. No. 5,023,387 to West et al.

The sudden expansion-type reactor was constructed and operated in the same manner and under the same conditions as employed in the production scale reactors of Example 1.

Residual, unreacted chlorine was measured at the outlet of each reactor apparatus, and 390 parts per million of chlorine were found with the gas/liquid reactor apparatus as compared to 580 parts per million with the pilot plant scale sudden expansion-type reactor.

EXAMPLE 3

A comparison was made in this example between the second reactor apparatus of Example 1 and a modified, production-scale gas/liquid reactor apparatus having a d/D of 0.12, and in which the guide vanes were tabbed with rectangular tabs.

Residual, unreacted chlorine was measured at the outlet of the modified gas/liquid reactor apparatus at just over 5 parts per million, as compared to the 20 ppm seen with the second reactor apparatus of Example 1.

EXAMPLE 4

This example compares the residual unreacted chlorine levels produced from the pilot plant scale, sudden expansion-type reactor apparatus of Example 2, and from two pilot plant scale, modified sudden expansion-type reactor apparatus involving the same degree of expansion and operated in the same fashion, but including perforated plates in the feed pipe of such apparatus as shown in FIGS. 1 and 2. In a first modified apparatus, a single perforated plate having a free area of 20 percent is placed about 2 feed pipe diameters from the exit end of the feed pipe, while in the second of the two modified apparatus a second, substantially identical perforated plate is placed an additional about 2 feed pipe diameters upstream from the first plate.

The unreacted chlorine from the first and second modified reactors was measured at 200 ppm and 140 ppm, respectively, as compared to the 580 ppm observed previously with the pilot-plant scale apparatus of Example 2.

One can conclude from the Examples as a whole that a significant reduction in residual (unreacted) chlorine may be obtained by using the apparatus of the present invention, as compared to those levels of residual chlorine produced in a conventional, unmodified sudden expansion-type chlorination reactor under the same conditions.

What is claimed is:

1. A process for enhancing the entrainment, adjacent the entry of a premixed stream of chlorine and one or more organic reactants selected from the group consisting of hydrocarbons and chlorinated hydrocarbons in a feed pipe into a thermally-initiated, adiabatic vapor-phase chlorination reactor vessel of the sudden expansion-type, of at least partly-reacted materials in said incoming premixed stream, comprising disrupting the flow pattern of the incoming stream of reactants at a distance of 0.5 to 5 feed pipe diameters upstream of the entry of said reactant stream into the reactor vessel.

2. A process as defined in claim 1, wherein the incoming reactant stream is comprised of chlorine, methyl chloride and methylene chloride.

3. A process as defined in claim 1, wherein the flow pattern of the incoming stream of reactants is disrupted without a significant increase in the pressure drop from the reactants' entry to the reactants' exit from the vessel.

4. A process as defined in claim 1, wherein the flow pattern of the incoming stream of reactants is disrupted in a substantially uniform manner over a cross-section of said stream.

5. A process as defined in claim 1, wherein the incoming stream of reactants is characterized by a Reynolds number at the entry of the reactant stream into the reactor of at least about 100,000.

* * * * *